United States Patent
Themens et al.

(10) Patent No.: US 8,932,611 B2
(45) Date of Patent: Jan. 13, 2015

(54) COSMETIC COMPOSITION CONTAINING ELASTOMERS

(75) Inventors: Agnès Themens, Bourg la Reine (FR); Maïtena Leuridan, Brie Comte Robert (FR)

(73) Assignee: L'Oreal, Paris (FR)

( * ) Notice: Subject to any disclaimer, the term of this patent is extended or adjusted under 35 U.S.C. 154(b) by 992 days.

(21) Appl. No.: 11/907,424

(22) Filed: Oct. 12, 2007

(65) Prior Publication Data
US 2009/0068238 A1 Mar. 12, 2009

Related U.S. Application Data

(60) Provisional application No. 60/851,753, filed on Oct. 16, 2006.

(30) Foreign Application Priority Data

Oct. 12, 2006 (FR) ...................................... 06 54214

(51) Int. Cl.
- A61K 8/02 (2006.01)
- A61K 8/89 (2006.01)
- A61Q 1/00 (2006.01)
- A61K 8/895 (2006.01)
- A61K 8/891 (2006.01)
- A61Q 1/02 (2006.01)

(52) U.S. Cl.
CPC ................. A61K 8/895 (2013.01); A61K 8/891 (2013.01); A61Q 1/02 (2013.01)
USPC ...................................... 424/401; 424/78.37

(58) Field of Classification Search
None
See application file for complete search history.

(56) References Cited

U.S. PATENT DOCUMENTS

| | | |
|---|---|---|
| 2003/0108498 A1 * | 6/2003 | Stephens et al. ................. 424/63 |
| 2005/0191328 A1 * | 9/2005 | Taniguchi ..................... 424/401 |
| 2005/0265943 A1 | 12/2005 | Geffroy-Hyland et al. |
| 2005/0287092 A1 * | 12/2005 | Liechty et al. .................. 424/63 |

FOREIGN PATENT DOCUMENTS

| | | | |
|---|---|---|---|
| EP | 1 550 687 | | 7/2005 |
| JP | 2006-069902 | * | 3/2006 |
| WO | WO 02/03935 | | 1/2002 |
| WO | WO 2004/054524 | * | 7/2004 |

OTHER PUBLICATIONS

Shin-Etsu Silicones for Personal Care Product Brochure for KSP, Mar. 2004. http://www.shinetsusilicones.com/files/KSP.pdf.*
French Search Report for FR 06/54214, dated May 11, 2007.

* cited by examiner

*Primary Examiner* — Scott Long
*Assistant Examiner* — Sarah Alawadi
(74) *Attorney, Agent, or Firm* — Oblon, Spivak, McClelland, Maier & Neustadt, L.L.P.

(57) ABSTRACT

The present invention relates to a solid anhydrous cosmetic composition comprising at least one non-spherical silicone elastomer and at least one silicone elastomer powder coated with a silicone resin. The invention also relates to a makeup process comprising the application to keratin materials of the said composition, and also to its use for obtaining a uniform makeup result that shows good fastness of the color over time.

21 Claims, No Drawings

COSMETIC COMPOSITION CONTAINING ELASTOMERS

This application claims benefit of U.S. Provisional Application No. 60/851,753, filed Oct. 16, 2006, the contents of which are incorporated herein by reference. This application also claims benefit of priority under 35 U.S.C. §119 to French Patent Application No. FR 06/54214, filed Oct. 12, 2006, the contents of which are also incorporated herein by reference.

The present invention relates to an anhydrous cosmetic composition, for example in "hot-cast" form, comprising silicone elastomers and at least one low molecular weight hydrocarbon-based ester oil. The composition may be a makeup or care composition for keratin materials such as the skin, the eyelids or the lips, and in at least one embodiment, for the skin. The invention also relates to a process for making up or caring for keratin materials.

Makeup compositions containing a fatty phase are commonly used in cosmetics on account of their good adhesion to the epidermis, their protecting capacity and their capacity to form a water-impermeable film. The makeup obtained is comfortable and does not dry out the skin.

Anhydrous makeup products are generally in solid, cast or compacted form, or alternatively in cream form. Compositions in "hot-cast" form may be desired as they may be applied satisfactorily using the fingers or an applicator, from packaging in the form of a dish or a stick. They generally contain oils and waxes that give them stable consistency over time.

However, due to their high content of fatty substances, products of this type may have the drawback of giving the skin a greasy, tacky feel. In addition, on account of their high content of waxes and solid particles, cast compositions may have hard textures, and be difficult to spread. The makeup result obtained is then non-uniform.

To improve the spreading of these compositions during their application to the skin, it is known practice to introduce oils, and to reduce the content of waxes and/or solid particles in order to obtain more supple textures. However, the introduction of these oils may lead to problems of stability of the compositions.

Thus, it would be desirable to provide a solid anhydrous composition, e.g., in the form of a cast product, which has good spreading properties that give the user sufficient time to apply the cosmetic product to the keratin materials on the skin during its application, without giving a greasy and tacky feel when applied.

The present inventors have demonstrated that by combining, in a solid anhydrous cosmetic composition, at least one non-spherical silicone elastomer and a spherical silicone elastomer powder, it is possible to obtain a stable solid composition with a creamy texture, which spreads well when applied to the skin, without giving the user a greasy feel.

The makeup result obtained is generally uniform and shows good fastness of the color over time. The composition generally does not dry out the skin and the deposit obtained is comfortable to the user.

According to a first aspect, one subject of the present invention is thus a solid anhydrous cosmetic composition comprising at least one non-spherical silicone elastomer and at least one silicone elastomer powder coated with a silicone resin.

According to a second aspect, a subject of the invention is a process for making up keratin materials, such as the skin, comprising the application to the keratin materials of at least one composition as described above.

According to a third aspect, a subject of the invention is the use of a composition as described above for obtaining a uniform makeup result that shows good fastness of the color over time.

A subject of the present invention is also a solid anhydrous cosmetic composition comprising:
at least one silicone elastomer corresponding to the INCI name "dimethicone/vinyl dimethicone crosspolymer",
at least one silicone elastomer powder corresponding to the INCI name "dimethicone/methicone silsesquioxane crosspolymer",
optionally at least one ester oil, and/or
optionally at least one wax.

The compositions according to the invention are solid compositions. For the purposes of the present disclosure, the term "solid composition" means a composition that does not flow under its own weight.

The compositions according to the present invention are anhydrous compositions.

For the purposes of the present disclosure, the term "anhydrous composition" means a composition comprising less than 5% by weight of water, such as less than 2% by weight of water relative to the total weight of the composition. In another embodiment, the composition is water-free, the water not being added during the preparation of the composition, but corresponding to the residual water provided by the mixed ingredients.

Non-Spherical Silicone Elastomers

The composition according to the invention comprises at least one non-spherical silicone elastomer. The silicone elastomer may be non-emulsifying or emulsifying.

According to one embodiment, the silicone elastomer is non-emulsifying.

The term "non-emulsifying" silicone elastomers defines organopolysiloxane elastomers not containing a hydrophilic chain, such as polyoxyalkylene or polyglycerolated units.

The non-emulsifying silicone elastomer is an elastomeric crossbonded organopolysiloxane that may be obtained by crosslinking addition reaction of diorganopolysiloxane containing at least one hydrogen bonded to silicon and of diorganopolysiloxane containing ethylenically unsaturated groups bonded to silicon, for example in the presence of a platinum catalyst; or by dehydrogenation crosslinking coupling reaction between a diorganopolysiloxane with hydroxyl end groups and a diorganopolysiloxane containing at least one hydrogen bonded to silicon, for example in the presence of an organotin compound; or by crosslinking coupling reaction of a diorganopolysiloxane with hydroxyl end groups and of a hydrolysable organopolysilane; or by thermal crosslinking of organopolysiloxane, for example in the presence of an organoperoxide catalyst; or by crosslinking of organopolysiloxane via high-energy radiation such as gamma rays, ultraviolet rays or an electron beam.

In at least one embodiment, the elastomeric crossbonded organopolysiloxane is obtained by crosslinking addition reaction (A2) of diorganopolysiloxane containing at least two hydrogens each bonded to a silicon, and (B2) of diorganopolysiloxane containing at least two ethylenically unsaturated groups bonded to silicon, for example in the presence (C2) of a platinum catalyst, as described, for example, in European Patent Application EP-A-295 886.

In at least one embodiment, the organopolysiloxane may be obtained by reaction of dimethylpolysiloxane with dimethylvinylsiloxy end groups and of methylhydrogenopolysiloxane with trimethylsiloxy end groups, in the presence of a platinum catalyst.

Compound (A2) is the base reagent for the formation of elastomeric organopolysiloxane, and the crosslinking is performed by addition reaction of compound (A2) with compound (B2) in the presence of the catalyst (C2).

Compound (A2) is advantageously a diorganopolysiloxane containing at least two lower (for example C2-C4) alkenyl groups; the lower alkenyl group may be chosen from vinyl, allyl and propenyl groups. These lower alkenyl groups may be located in any position on the organopolysiloxane molecule, but are, for example, located at the ends of the organopolysiloxane molecule. The organopolysiloxane (A2) may have a branched-chain, linear-chain, cyclic or network structure, but the linear-chain structure is used in at least one embodiment. Compound (A2) may have a viscosity ranging from the liquid state to the gum state. In at least one embodiment, compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes with dimethylvinylsiloxy end groups, dimethylsiloxane-methylphenylsiloxane copolymers with dimethylvinylsiloxy end groups, dimethylsiloxane-diphenylsiloxane-methylvinylsiloxane copolymers with dimethylvinylsiloxy end groups, dimethylsiloxane-methylvinylsiloxane copolymers with trimethylsiloxy end groups, dimethylsiloxane-methylphenylsiloxane-methyl-vinylsiloxane copolymers with trimethylsiloxy end groups, methyl(3,3,3-trifluoro-propyl)polysiloxanes with dimethylvinylsiloxy end groups, and dimethylsiloxane-methyl(3,3,3-trifluoropropyl)siloxane copolymers with dimethylvinylsiloxy end groups.

Compound (B2) is, for example, an organopolysiloxane containing at least two hydrogens bonded to silicon in each molecule and is thus the crosslinking agent for compound (A2).

In at least one embodiment, the sum of the number of ethylenic groups per molecule of compound (A2) and the number of hydrogen atoms bonded to silicon per molecule of compound (B2) is at least 4.

Compound (B2) may be in any molecular structure, for example, linear-chain or branched-chain structure, or cyclic structure.

Compound (B2) may have a viscosity at 25° C. ranging from 1 to 50 000 centistokes, for example in order to have good miscibility with compound (A).

In at least one embodiment, compound (B2) is added in an amount such that the molecular ratio between the total amount of hydrogen atoms bonded to silicon in compound (B2) and the total amount of all of the ethylenically unsaturated groups in compound (A2) is within the range from 1/1 to 20/1.

Compound (B2) may be chosen from methylhydrogenopolysiloxanes with trimethylsiloxy end groups, dimethylsiloxane-methylhydrogenosiloxane copolymers with trimethylsiloxy end groups, and dimethylsiloxane-methylhydrogenosiloxane cyclic copolymers.

Compound (C2) is the crosslinking reaction catalyst, and is, for example, chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is, for example, added in from 0.1 to 1000 parts by weight, such as from 1 to 100 parts by weight, as clean platinum metal per 1000 parts by weight of the total amount of compounds (A2) and (B2).

Other organic groups may be bonded to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

According to one embodiment, the non-emulsifying silicone elastomer is mixed with at least one hydrocarbon-based oil and/or one silicone oil to form a gel. In these gels, the non-emulsifying elastomer is in the form of non-spherical particles.

Non-emulsifying elastomers that may be used include those sold under the names KSG-6, KSG-15, KSG-16, KSG-18, KSG-31, KSG-32, KSG-33, KSG-41, KSG-42, KSG-43 and KSG-44 by the company Shin-Etsu, DC9040, DC9041, DC9509, DC9505 and DC9506 by the company Dow Corning, Gransil by the company Grant Industries, and SFE 839 by the company General Electric.

The non-spherical silicone elastomer may be emulsifying.

The term "emulsifying silicone elastomer" as used herein means a silicone elastomer comprising at least one hydrophilic chain.

The emulsifying silicone elastomer may be chosen from polyoxyalkylenated silicone elastomers.

The polyoxyalkylenated silicone elastomer is a crossbonded organopolysiloxane that may be obtained by crosslinking addition reaction of diorganopoly-siloxane containing at least one hydrogen bonded to silicon and of a polyoxyalkylene containing at least two ethylenically unsaturated groups.

In at least one embodiment, the polyoxyalkylenated crossbonded organo-polysiloxane is obtained by crosslinking addition reaction (A1) of diorganopolysiloxane containing at least two hydrogens each bonded to a silicon, and (B1) of polyoxyalkylene containing at least two ethylenically unsaturated groups, for example in the presence (C1) of a platinum catalyst, as described, for example, in U.S. Pat. No. 5,236,986 and U.S. Pat. No. 5,412,004.

In at least one embodiment, the organopolysiloxane may be obtained by reaction of polyoxyalkylene (especially polyoxyethylene and/or polyoxypropylene) with dimethylvinylsiloxy end groups and of methylhydrogenopolysiloxane with trimethylsiloxy end groups, in the presence of a platinum catalyst.

The organic groups bonded to silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes with trimethylsiloxy end groups, dimethylsiloxane-methylhydrogenosiloxane copolymers with trimethylsiloxy end groups, dimethylsiloxane-methylhydrogenosiloxane cyclic copolymers, or dimethylsiloxane-methylhydrogenosiloxane-laurylmethylsiloxane copolymers with trimethylsiloxy end groups.

Compound (C1) is the crosslinking reaction catalyst, and is, for example, chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, such as polyoxyalkylenes containing at least two vinyl groups, reacting with Si—H bonds of a polysiloxane.

The polyoxyalkylenated silicone elastomer according to the invention is brought into gel form with at least one hydrocarbon-based oil and/or one silicone oil. In these gels, the polyoxyalkylenated elastomer is in the form of non-spherical particles.

Polyoxyalkylenated elastomers are, for example, described in U.S. Pat. No. 5,236,986, U.S. Pat. No. 5,412,004, U.S. Pat. No. 5,837,793 and U.S. Pat. No. 5,811,487, the disclosures of which are incorporated by reference.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, or DC9010 and DC9011 by the company Dow Corning.

The emulsifying silicone elastomer may also be chosen from polyglycerolated silicone elastomers.

The polyglycerolated silicone elastomer is an elastomeric crossbonded organopolysiloxane that may be obtained by crosslinking addition reaction of diorganopolysiloxane containing at least one hydrogen bonded to silicon and of polyglycerolated compounds containing ethylenically unsaturated groups, for example in the presence of a platinum catalyst.

In at least one embodiment, the elastomeric crossbonded organopolysiloxane is obtained by crosslinking addition reaction (A) of diorganopolysiloxane containing at least two hydrogens each bonded to a silicon, and (B) of glycerolated compounds containing at least two ethylenically unsaturated groups, for example in the presence (C) of a platinum catalyst.

In at least one embodiment, the organopolysiloxane may be obtained by reaction of a polyglycerolated compound with dimethylvinylsiloxy end groups and of methylhydrogenopolysiloxane with trimethylsiloxy end groups, in the presence of a platinum catalyst.

Compound (A) is the base reagent for the formation of elastomeric organopolysiloxane and the crosslinking is performed by addition reaction of compound (A) with compound (B) in the presence of the catalyst (C).

Compound (A) is, for example, an organopolysiloxane containing at least two hydrogen atoms bonded to different silicon atoms in each molecule.

Compound (A) may have any molecular structure, for example a linear chain or branched chain structure or a cyclic structure.

Compound (A) may have a viscosity at 25° C. ranging from 1 to 50 000 centistokes, e.g., in order to have good miscibility with compound (B).

The organic groups bonded to silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. The organic group is, in one embodiment, chosen from methyl, phenyl and lauryl groups.

Compound (A) may thus be chosen from methylhydrogenopolysiloxanes with trimethylsiloxy end groups, dimethylsiloxane-methylhydrogenosiloxane copolymers with trimethylsiloxy end groups, dimethylsiloxane-methylhydrogenosiloxane cyclic copolymers, or dimethylsiloxane-methylhydrogenosiloxane-laurylmethylsiloxane copolymers with trimethylsiloxy end groups.

Compound (B) may be a polyglycerolated compound corresponding to formula (B') below:

  (B')

in which:

m is an integer ranging from 2 to 6, n is an integer ranging from 2 to 200, such as ranging from 2 to 100, for example ranging from 2 to 50, such as n ranging from 2 to 20, or 2 to 10 or 2 to 5, and in one embodiment, equal to 3; Gly denotes:

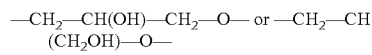

In at least one embodiment, the sum of the number of ethylenic groups per molecule of compound (B) and of the number of hydrogen atoms bonded to silicon atoms per molecule of compound (A) is at least 4.

In at least one embodiment, compound (A) is added in an amount such that the molecular ratio between the total amount of hydrogen atoms bonded to silicon atoms in compound (A) and the total amount of all the ethylenically unsaturated groups in compound (B) is within the range from 1/1 to 20/1.

Compound (C) is the crosslinking reaction catalyst, and is, for example, chloroplatinic acid, chloroplatinic acid-olefin complexes, chloroplatinic acid-alkenylsiloxane complexes, chloroplatinic acid-diketone complexes, platinum black and platinum on a support.

The catalyst (C) is, in at least one embodiment, added in from 0.1 to 1000 parts by weight, such as from 1 to 100 parts by weight, as clean platinum metal per 1000 parts by weight of the total amount of compounds (A) and (B).

The polyglycerolated silicone elastomer according to the invention is generally mixed with at least one hydrocarbon-based oil and/or one silicone oil to form a gel. In these gels, the polyglycerolated elastomer is often in the form of non-spherical particles.

Such elastomers are described, for example, in International Patent Application WO 2004/024798.

Polyglycerolated silicone elastomers that may be used include those sold under the names KSG-710, KSG-810, KSG-820, KSG-830 and KSG-840 by the company Shin-Etsu.

According to one embodiment, the composition according to the invention comprises at least one non-emulsifying non-spherical silicone elastomer mixed with at least one hydrocarbon-based oil and/or one silicone oil to form a gel.

The non-spherical silicone elastomer may be present in the composition according to the invention in an active material content ranging from 0.01% to 8% by weight, such as ranging from 2% to 7% by weight and, or from 3% to 6% by weight relative to the total weight of the composition.

Silicone Elastomer Powder Coated with a Silicone Resin

The composition according to the invention comprises at least one silicone elastomer powder coated with a silicone resin. The silicone elastomer powder is spherical.

In at least one embodiment, the silicone elastomer in powder form is non-emulsifying. It may be obtained, for example, via the processes for synthesizing non-emulsifying elastomers described above.

Spherical elastomeric organopolysiloxanes are, for example, described in patent applications JP-A-61-194 009, EP-A-242 219, EP-A-295 886 and EP-A-765 656, the disclosures of which are incorporated herein by way of reference.

Elastomeric organopolysiloxane powders that may be used include those sold under the names Dow Corning 9505 Powder and Dow Corning 9506 Powder by the company Dow Corning; these powders have the INCI name: dimethicone/vinyl dimethicone crosspolymer.

The silicone elastomer powder is coated with silicone resin.

According to one embodiment, the silicone resin may be a silsesquioxane resin, as described, for example, in U.S. Pat. No. 5,538,793, the content of which is incorporated herein by way of reference.

Such elastomer powders coated with silicone resin are, for example, sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

Such powders correspond to the INCI name dimethicone silsesquioxane crosspolymer, and in particular vinyl dimethicone/methicone silsesquioxane crosspolymer.

According to another embodiment, the elastomeric organopolysiloxanes in spherical powder form may be powders of hybrid silicone functionalized with fluoroalkyl groups, especially sold under the name KSP-200 by the company Shin-Etsu; powders of hybrid silicone functionalized with phenyl groups, e.g., sold under the name KSP-300 by the company Shin-Etsu.

The silicone elastomer particles may have a JIS-A hardness of less than or equal to 80 (for example ranging from 5 to 80) and, in one embodiment, less than or equal to 65 (for example ranging from 5 to 65). The JIS-A hardness is measured according to the method JIS K 6301 (1995) established by the Japanese Industrial Standards Committee.

In at least one embodiment, the silicone elastomer particles may have a mean size ranging from 0.1 to 500 μm, such as from 3 to 200 μm, or from 10 to 20 μm. These particles may be of spherical, flat or amorphous shape, such as of spherical shape.

The silicone elastomer powder coated with a silicone resin, which is, for example, non-emulsifying, and, in at least one embodiment, spherical, may be present in the composition in a content ranging from 0.5% to 8% by weight, such as ranging from 1% to 6% by weight relative to the total weight of the composition.

Besides the non-spherical silicone elastomer(s) and the silicone elastomer powder(s) coated with a silicone resin, the composition according to the invention may comprise another silicone elastomer, e.g., a silicone elastomer powder not coated with a silicone resin, such as Dow Corning 9505 Powder or Dow Corning 9506 Powder by the company Dow Corning, described previously, or alternatively those described in document JP-A-02-243 612, such as those sold under the name Trefil Powder E-506C by the company Dow Corning.

Low Molecular Weight Hydrocarbon-Based Ester Oil

The composition according to the invention may comprise at least one low molecular weight hydrocarbon-based ester oil, also referred to as a "short ester".

For the purposes of the present disclosure, the term "low molecular weight hydrocarbon-based ester oil" means a hydrocarbon-based ester containing less than 40 carbon atoms. Such esters, when they are introduced into the compositions according to the invention, make it possible to further improve the spreadability of the product onto keratin materials.

The esters in accordance with the invention may be monoesters, diesters or polyesters and are, in at least one embodiment, monoesters, i.e., bearing only one ester function. These esters may be linear, branched or cyclic, and saturated or unsaturated. In at least one embodiment, they are branched and saturated. They may also be volatile or non-volatile.

In at least one embodiment, the hydrocarbon-based esters may correspond to the formula RCOOR' in which RCOO represents a fatty acid residue containing from 2 to 28 carbon atoms and R' represents a hydrocarbon-based chain containing from 1 to 28 carbon atoms. In a further embodiment, the groups R and R' are such that the corresponding ester is non-volatile.

In at least one embodiment, the monoester, diester or polyester hydrocarbon-based esters, which may be used in the cosmetic compositions in accordance with the invention, contain less than 40 carbon atoms and more than 10 carbon atoms.

These non-volatile esters may, for example, be of $C_{10}$ to $C_{26}$, such as of $C_{14}$ to $C_{24}$. They may be chosen from esters of $C_2$ to $C_{18}$ acids and, for example, of $C_2$ to $C_{20}$ alcohols or of $C_2$ to $C_8$ polyols, or mixtures thereof.

In one embodiment, they contain less than 25 carbon atoms.

According to one embodiment, when the hydrocarbon-based ester contains less than 25 carbon atoms, it is not a volatile oil.

Thus, the esters may be chosen from a non-limiting list comprising neopentanoic acid esters, for instance isodecyl neopentanoate, isotridecyl neopentanoate, isostearyl neopentanoate, octyldodecyl neopentanoate, isononanoic acid esters, for instance isononyl isononanoate, octyl isononanoate, isodecyl isononanoate, isotridecyl isononanoate or isostearyl isononanoate, but also isopropyl alcohol esters, such as isopropyl myristate, isopropyl palmitate, isopropyl stearate or isostearate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof. The said ester may also be chosen from synthetic esters, for example of fatty acid, for instance purcellin oil, isopropyl myristate, ethyl palmitate or octyl stearate; hydroxylated esters, for instance isostearyl lactate, octyl hydroxystearate or diisopropyl adipate, and fatty alkyl heptanoates, octanoates or decanoates, and mixtures thereof.

According to one embodiment, the short hydrocarbon-based ester used in the cosmetic composition in accordance with the present invention may be chosen from isononyl isononanoate and 2-ethylhexyl palmitate, and a mixture thereof.

According to another embodiment, the composition according to the invention comprises at least two short esters of different nature, for example a mixture of isononyl isononanoate and of 2-ethylhexyl palmitate.

This or these hydrocarbon-based ester(s) may be used in the composition in a content ranging from 10% to 60% by weight, for example from 20% to 55% by weight, such as from 30% to 50% by weight relative to the total weight of the composition.

Additional Oils

Besides the low molecular weight hydrocarbon-based ester oil, the composition according to the invention may comprise an additional oil chosen from volatile oils and non-volatile oils, and a mixture thereof.

According to one embodiment, the composition according to the invention may comprise at least one additional non-volatile oil, different from the low molecular weight hydrocarbon-based ester oil and from the oil used to form a non-spherical elastomer gel.

The term "non-volatile oil" as used herein means an oil that remains on the skin at room temperature and atmospheric pressure for at least several hours and that, for example, has a vapor pressure of less than 0.13 Pa (0.01 mmHg) at room temperature (25° C.).

Non-volatile hydrocarbon-based oils that may be mentioned include, for example:

hydrocarbon-based oils of animal origin, hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are, e.g., heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stéarineries Dubois or those sold under the names Miglyol 810®, 812® and 818® by the company Dynamit Nobel, linear or branched hydrocarbons of mineral or synthetic origin, such as petroleum jelly, polydecenes, hydrogenated polyisobutene such as Parleam®, squalane and liquid paraffins, and mixtures thereof, synthetic esters containing more than 40 carbon atoms, fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, higher fatty acids such as oleic acid, linoleic acid or linolenic acid, and mixtures thereof.

According to one embodiment, the composition according to the invention may comprise at least one additional non-volatile silicone oil.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones and diphenylmethyldiphenyltrisiloxanes, and mixtures thereof.

The composition according to the invention may also comprise at least one additional volatile oil, different from the low molecular weight hydrocarbon-based ester oil and from the oil used to form a non-spherical elastomer gel.

For the purposes of the invention, the term "volatile oil" means any oil that is capable of evaporating on contact with the skin, at room temperature and atmospheric pressure. The volatile oils of the invention are volatile cosmetic oils that are liquid at room temperature, with a non-zero vapor pressure at room temperature and atmospheric pressure, ranging, for example, from 0.13 Pa to 40 000 Pa (0.001 to 300 mmHg), such as ranging from 1.3 Pa to 1300 Pa (0.01 to 10 mmHg).

The volatile oil may be chosen from volatile hydrocarbon-based oils, volatile silicone oils and volatile fluoro oils, and mixtures thereof.

The term "hydrocarbon-based oil" as used herein means an oil mainly containing hydrogen and carbon atoms and possibly oxygen, nitrogen, sulfur and/or phosphorus atoms.

The volatile hydrocarbon-based oils may be chosen from hydrocarbon-based oils containing from 8 to 16 carbon atoms, for example branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isohexadecane and, for example, the oils sold under the trade names Isopar® and Permethyl®.

Volatile oils that may also be used include volatile silicones, for instance volatile linear or cyclic silicone oils, e.g., those with a viscosity ≤5 centistokes ($5\times10^{-6}$ m$^2$/s) and containing from 2 to 10 silicon atoms, such as from 2 to 7 silicon atoms, these silicones optionally comprising alkyl or alkoxy groups containing from 1 to 10 carbon atoms. As volatile silicone oils that may be used in the invention, mention may be made, for example, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The volatile fluoro oil generally does not have a flash point.

Volatile fluoro oils that may be mentioned include nonafluoroethoxybutane, nonafluoromethoxybutane, decafluoropentane, tetradecafluorohexane and dodeca-fluoropentane, and mixtures thereof.

According to one embodiment, the composition comprises no additional volatile silicone oil.

In at least one embodiment, the composition is free of additional volatile oils.

In another embodiment, the composition comprises less than 5% by weight of volatile oils, such as less than 2% by weight of water, relative to the total weight of the composition.

Waxes

The composition according to the invention may comprise at least one wax.

For the purposes of the present disclosure, the term "wax" means a lipophilic fatty compound, which is solid at room temperature (25° C.) and atmospheric pressure (760 mmHg, i.e. $10^5$ Pa) which undergoes a reversible solid/liquid change of state, and which, in at least one embodiment has a melting point of greater than or equal to 30° C., such as greater than or equal to 55° C., which may be up to 250° C., or up to 230° C., such as up to 120° C.

By bringing the wax to its melting point, it is possible to make it miscible with the oils and to form a microscopically homogeneous mixture, but on returning the temperature of the mixture to room temperature, recrystallization of the wax in the oils of the mixture is obtained.

According to the present disclosure, the melting point values correspond to the melting peak measured using a differential scanning calorimeter (DSC), for example the calorimeter sold under the name DSC 30 by the company Mettler, with a temperature rise of 5 or 10° C. per minute.

For the purposes of the present disclosure, the waxes may be those generally used in cosmetics or dermatology. They may, in at least one embodiment, be hydrocarbon-based waxes, silicone waxes and/or fluoro waxes, optionally comprising ester or hydroxyl functions. They may also be of natural or synthetic origin.

Non-limiting illustrations of these waxes that may especially be mentioned include:

beeswax, lanolin wax and Chinese insect waxes; rice wax, carnauba wax, candelilla wax, ouricury wax, cork fibre wax, sugarcane wax, Japan wax and sumach wax; montan wax; microcrystalline waxes, paraffin waxes, ozokerites, ceresin wax, lignite wax, polyethylene waxes, the waxes obtained by Fisher-Tropsch synthesis, and fatty acid esters and glycerides that are solid at 40° C. and especially above 55° C., the waxes obtained by catalytic hydrogenation of animal or plant oils containing linear or branched $C_8$-$C_{32}$ fatty chains, e.g., hydrogenated jojoba oil, hydrogenated sunflower oil, hydrogenated castor oil, hydrogenated coconut oil and hydrogenated lanolin oil, silicone waxes or fluoro waxes, and mixtures thereof.

According to one embodiment of the invention, the wax may be chosen from carnauba waxes and microcrystalline waxes, and mixtures thereof.

The wax(es) may be present in the composition according to the invention in a content ranging from 1% to 15% by weight, such as from 2% to 12% by weight, for example from 5% to 9% by weight relative to the total weight of the composition.

Besides the waxes described previously, the compositions according to the invention may also comprise additional fatty substances such as pasty fatty substances.

Dyestuffs

According to one embodiment of the invention, the composition may comprise at least one dyestuff.

For the purposes of the present disclosure, the term "dyestuff" means a compound capable of producing a colored optical effect when it is formulated in sufficient amount in a suitable cosmetic medium.

The dyestuff may be chosen, for instance, from pulverulent dyestuffs, liposoluble dyes and water-soluble dyes, and mixtures thereof.

The pulverulent dyestuffs may be chosen from pigments, nacres and flakes, and mixtures thereof.

According to one embodiment of the invention, the dyestuff may comprise at least one pulverulent dyestuff chosen from pigments and nacres, and a mixture thereof.

The pigments may be chosen from mineral pigments, organic pigments and composite pigments (i.e. pigments based on mineral and/or organic materials).

The term "pigments" as used herein should be understood as meaning mineral or synthetic particles of any form, endowed with an optical effect, which are insoluble in the medium of the composition irrespective of the temperature at which the composition is manufactured.

The pigments may be chosen from monochromatic pigments, lakes, nacres and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

The organic pigments may be, for example:

cochineal carmine;

organic pigments of azo dyes, anthraquinone dyes, indigoid dyes, xanthene dyes, pyrene dyes, quinoline dyes, triphenylmethane dyes or fluorane dyes;

organic lakes or insoluble salts of sodium, potassium, calcium, barium, aluminium, zirconium, strontium or titanium, or of acidic dyes such as azo dyes, anthraquinone dyes, indigoid dyes, xanthene dyes, pyrene dyes, quinoline dyes, triphenylmethane dyes or fluorane dyes. These dyes generally comprise at least one carboxylic or sulfonic acid group;

melanin pigments.

Among the organic pigments that may be mentioned are D&C Blue No 4, D&C Brown No 1, D&C Green No 5, D&C Green No 6, D&C Orange No 4, D&C Orange No 5, D&C Orange No 10, D&C Orange No 11, D&C Red No 6, D&C Red No 7, D&C Red No 17, D&C Red No 21, D&C Red No 22, D&C Red No 27, D&C Red No 28, D&C Red No 30, D&C Red No 31, D&C Red No 33, D&C Red No 34, D&C Red No 36, D&C Violet No 2, D&C Yellow No 7, D&C Yellow No 8, D&C Yellow No 10, D&C Yellow No 11, FD&C Blue No 1, FD&C Green No 3, FD&C Red No 40, FD&C Yellow No 5 and FD&C Yellow No 6.

The hydrophobic-treatment agent may be chosen from silicones, for instance methicones, dimethicones or perfluoroalkylsilanes; fatty acids, for instance stearic acid; metal soaps, for instance aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, and amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds mentioned above denotes an alkyl group containing from 1 to 30 carbon atoms, such as containing from 5 to 16 carbon atoms.

Hydrophobic-treated pigments are described, for example, in European patent application EP-A-1 086 683.

For the purposes of the present disclosure, the term "nacre" should be understood as meaning colored particles of any form, which may or may not be iridescent, e.g., produced by certain molluscs in their shell, or alternatively synthesized, and which have a color effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may, for example, have a yellow, pink, red, bronze, orange, brown, gold and/or coppery color or tint.

As illustrations of nacres that may be introduced as interference pigments into the first composition, mention may be made, in at least one embodiment, of the gold-colored nacres sold especially by the company Engelhard under the name Brillant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The pulverulent dyestuffs may be present in the composition according to the invention in a content ranging from 1% to 40% by weight, such as from 5% to 30% by weight and for example from 10% to 25% by weight relative to the total weight of the composition.

The water-soluble or liposoluble dyestuffs may be chosen from liposoluble dyes and water-soluble dyes, and a mixture thereof.

The liposoluble dyes are, for example, Sudan Red, D&C Red No 17, D&C Green No 6, β-carotene, soybean oil, Sudan Brown, D&C Yellow No 11, D&C Violet No 2, D&C Orange No 5, quinoline yellow, annatto and bromo acids.

The water-soluble dyes are, for example, beetroot juice, methylene blue and caramel.

Fillers

The composition according to the invention may comprise at least one filler.

The term "fillers" as used herein should be understood as meaning colorless or white, mineral or synthetic particles of any form, which are insoluble in the medium of the composition irrespective of the temperature at which the composition is manufactured.

The fillers may be mineral or organic and of any form, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powders, poly-β-alanine powders, polyethylene powders, polymethyl methacrylates, polyurethane powders such as the powder of the copolymer of hexamethylene diisocyanate and of trimethylol hexyl lactone sold under the name Plastic Powder D-400 by the company Toshiki, tetrafluoroethylene polymer (Teflon®) powders, lauroyllysine, starch, boron nitride, polyvinylidene chloride/acrylonitrile copolymers, acrylic acid copolymers, silicone resin powders, in particular silsesquioxane powders (silicone resin powders described especially in patent EP 293795; for example Tospearls® from Toshiba), elastomeric polyorganosiloxane particles, precipitated calcium carbonate, magnesium carbonate, magnesium hydrogen carbonate, hydroxyapatite, hollow silica microspheres, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate; barium sulfate, and mixtures thereof.

According to one embodiment, the composition according to the invention may comprise at least one spherical filler other than the resin-coated silicone elastomer powder, especially a polyamide (Nylon®)) powder.

Galenicals

The solid anhydrous compositions according to the invention may, in at least one embodiment, be compositions in "hot-cast" form.

For the purposes of the present disclosure, the expression "compositions in "hot-cast" form" means a solid composition obtained after cooling a composition introduced in melt form into a mold. The compositions may be cast in the form of a stick or wand, or into a dish.

Additives

The composition according to the invention may comprise at least one other common cosmetic ingredient, which may be chosen, for example, from lipophilic thickeners, antioxidants, fragrances, preserving agents, neutralizers, sunscreens, vitamins, moisturizers, self-tanning compounds, anti-wrinkle active agents, emollients, lipophilic active agents, anti-pollution agents or free-radical scavengers, sequestrants, film-forming agents, non-elastomeric surfactants, dermo-relaxing active agents, calmatives, agents for stimulating the synthesis of and/or for preventing the degradation of dermal or epidermal macromolecules, anti-glycation agents, anti-irritant agents, desquamating agents, depigmenting agents, anti-pigmenting or pro-pigmenting agents, NO-synthase inhibitors, agents for stimulating fibroblast or keratinocyte proliferation and/or keratinocyte differentiation, agents acting on the capillary circulation, agents acting on the energy metabolism of cells, and cicatrizing agents, and mixtures thereof.

Spreadability Protocol

The spreadability index of the composition according to the invention is determined according to the measuring protocol described below.

A support (square of 40 mm×40 mm) consisting of a layer of neoprene foam that is adhesive on one of its faces (sold under the name RE70X40 212B from the company Joint Technique Lyonnais Ind) is prepared. An adhesive crown having an inside diameter of 20 mm and a thickness of about 250 μm is fixed onto the non-adhesive face of the support. The composition is applied inside the crown and is leveled off with a glass slide to obtain a deposit of composition about 250 μm thick, and the crown is then removed without allowing any drying time.

The support is then bonded via its adhesive face to a tip 27 mm in diameter attached to a press (Statif Manuel SV-1 from the company Imada Co. Ltd.) equipped with a tensile testing machine (DPS-5R from the company Imada Co. Ltd.).

A strip 4 cm wide and 21 cm long is drawn on a photo-quality coated paper (reference Epson S041061 with a basis weight of 102 g/m$^2$) and 5 boxes each 4.2 cm long are drawn inside this strip in the longitudinal axis of the strip. The paper is placed on the bed of the press.

The support (comprising the sample of composition) is then pressed onto the first box of the strip of paper, with a force of about 1.5 kg exerted for 5 seconds. The paper is then displaced in a straight and uniform manner over the entire length of the strip such that the support comes into contact with the entire length of the strip. The displacement speed of the strip is about 10 cm/s.

The trail of product deposited on the strip of paper is then observed visually. The spreading properties of two compositions may thus be compared as a function of the number of boxes, from the first to the fifth, possibly totally or partially crossed by the trail of product.

By convention, the separation line between box n and box n+1 forms part of box n.

Measurement of Elastic Texture of the Composition

The penetration force is then measured on the composition at a temperature of 20° C. using a texturometer sold under the name TA-XT2 by the company Rheo, equipped with a "Mobile P10 Cylinder ebonite" measuring spindle. The measuring cell is programmed at 5 kg (which corresponds to the sensitivity of the machine, which can then measure forces up to 5 kg). The composition is introduced in molten form into a rectangular H377 dish 4.7 cm long, 3.9 cm wide and 0.5 cm high, and is left to cool for 24 hours at 20° C. (the composition obtained is thus in "hot-cast" form).

The spindle descends vertically at a speed (referred to as the pre-speed) of 1.0 mm/s. Measurement is started when the composition exerts on the spindle a force of 0.1 g (triggering force).

The spindle then continues to descend vertically into the composition at a penetration speed of 0.5 mm/s, down to a penetration depth of 0.5 mm.

The penetration force F1 is thus measured (maximum force recorded during the penetration).

The spindle is maintained at a depth of 0.5 mm for a relaxation time of 35 sec. After 35 sec, F2 is measured, which corresponds to the force exerted by the composition at the end of its relaxation (after 35 sec).

The spindle is then raised to its initial position at a speed (referred to as the post-speed) of 2.0 mm/s.

One measurement is taken at the centre of the dish, and three different dishes are tested. The penetration force F1 expressed in grams is read on the machine at each measurement, and a mean Fm1 is then calculated. The same process is followed for the relaxation force F2, of which the mean force Fm2 of the various measurements taken is calculated.

The elasticity EL of the product is calculated by means of the following relationship: EL=(Fm1−Fm2)/Fm1. The lower the value of EL, the greater the elastic texture of the composition.

The present invention is described in greater detail in the examples below.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are intended to illustrate the present disclosure without, however, being limiting in nature.

EXAMPLES 1 AND 2

"Hot-cast" foundations having the compositions below were prepared:

| Chemical name | Ex. 1 | Ex. 2 |
|---|---|---|
| Carnauba wax | 2.6 | 2.4 |
| Microcrystalline wax | 5.1 | 4.8 |
| Silicone elastomer gel containing 24% active material in a polydimethylsiloxane oil 6 cSt, sold under the name KSG-16 by the company Dow Corning | 15.0 | 14.1 |
| Crosslinked polydimethylsiloxane beads coated with polydimethylsilsesquioxane resin (92/8), sold under the name KSP-100 by the company Shin-Etsu | 2.0 | 1.9 |
| Nylon 12 | 6.0 | 5.7 |
| Titanium dioxide | 10.20 | 14.2 |
| Iron oxides | 3.8 | 4.9 |
| 2-Ethylhexyl palmitate | 8.6 | 8.1 |
| Isononyl isononanoate | 32.6 | 30.7 |
| Phenyl trimethicone | 9.0 | 8.5 |
| Preserving agents | qs | qs |
| Elasticity EL = (Fm1 − Fm2)/Fm1 | 0.64 | 0.58 |

EXAMPLE 3

Comparative

A "hot-cast" foundation outside the invention, having the composition below, was prepared:

| Chemical name | Comparative Ex. 3 |
|---|---|
| Carnauba wax | 2.6 |
| Microcrystalline wax | 5.1 |
| Polytetrafluoroethylene wax | 7.0 |
| Silicone elastomer gel containing 24% active material in a polydimethylsiloxane oil 6 cSt, sold under the name KSG-16 by the company Dow Corning | 0 |
| Crosslinked polydimethylsiloxane beads coated with polydimethylsilsesquioxane resin (92/8), sold under the name KSP-100 by the company Shin-Etsu | 0 |
| Nylon 12 | 16.0 |
| Nanotitanium oxide | 5.0 |
| Iron oxides | 14.0 |
| 2-Ethylhexyl palmitate | 6.9 |
| Isononyl isononanoate | 30.9 |
| Phenyl trimethicone | 7.4 |
| Preserving agents | qs |
| Elasticity EL = (Fm1 − Fm2)/Fm1 | 0.73 |

The spreading of compositions 1 and 3 was compared, by means of the protocol defined previously.

Comparative Example 3 leaves a shorter and less intense trail than Example 1 according to the invention. This indicates that the foundation according to the invention spreads better than the comparative foundation 3.

What is claimed is:

1. A solid anhydrous cosmetic composition comprising:
    at least one non-spherical silicone elastomer in an amount of 0.01 to 8% by weight based on the total weight of the composition,
    from 1 to 8% by weight, based on the total weight of the composition, of at least one spherical silicone elastomer powder coated with a silicone resin,
    at least one dyestuff,
    at least one wax in an amount of 5 to 9% by weight based on the total weight of the composition, and
    from 10 to 60% by weight at least one low molecular weight $C_{10}$ to $C_{25}$ ester oil,
    wherein the at least one non-spherical silicone elastomer, the at least one spherical silicone elastomer powder coated with a silicone resin, the at least one wax and the at least one low molecular weight $C_{10}$ to $C_{25}$ ester oil are present in combination to form a hot cast form that does not flow under its own weight and has a creamy texture.

2. A composition according to claim 1, wherein the at least one non-spherical silicone elastomer is chosen from those obtained by:
- a process comprising a crosslinking addition reaction of diorganosiloxane containing at least one hydrogen bonded to silicon and of a polyoxyalkylene containing at least two ethylenically unsaturated groups;
- a process comprising a crosslinking addition reaction of diorganosiloxane containing at least one hydrogen bonded to silicon and of polyglycerolated compounds containing ethylenically unsaturated groups, optionally in the presence of a platinum catalyst;
- a process comprising a crosslinking addition reaction of diorganosiloxane containing at least one hydrogen bonded to silicon and of diorganopolysiloxane containing ethylenically unsaturated groups bonded to silicon;
- a process comprising a dehydrogenation crosslinking coupling reaction between a diorganopolysiloxane with hydroxyl end groups and a diorganopolysiloxane containing at least one hydrogen bonded to silicon;
- a process comprising a crosslinking coupling reaction of a diorganopolysiloxane with hydroxyl end groups and of a hydrolysable organopolysilane;
- a process comprising a thermal crosslinking of organopolysiloxane;
- a process comprising a high-energy radiation crosslinking of organopolysiloxane.

3. A composition according to claim 2, wherein the at least one non-spherical silicone elastomer is obtained by a process comprising a crosslinking addition reaction (A) of diorganopolysiloxane containing at least two hydrogens each bonded to a silicon, and (B) of diorganopolysiloxane containing at least two ethylenically unsaturated groups bonded to silicon, optionally in the presence (C) of a platinum catalyst.

4. A composition according to claim 2, wherein the at least one non-spherical silicone elastomer is obtained by a process comprising a reaction of dimethylpolysiloxane with dimethylvinylsiloxy end groups and of methylhydrogenopolysiloxane with trimethylsiloxy end groups, in the presence of a platinum catalyst.

5. A composition according to claim 1, wherein the resin-coated silicone elastomer is chosen from those obtained by:
- a process comprising a crosslinking addition reaction of diorganosiloxane containing at least one hydrogen bonded to silicon and of diorganopolysiloxane containing ethylenically unsaturated groups bonded to silicon;
- a process comprising a dehydrogenation crosslinking coupling reaction between a diorganopolysiloxane with hydroxyl end groups and a diorganopolysiloxane containing at least one hydrogen bonded to silicon;
- a process comprising a crosslinking coupling reaction of a diorganopolysiloxane with hydroxyl end groups and of a hydrolysable organopolysilane;
- a process comprising a thermal crosslinking of organopolysiloxane;
- a process comprising a high-energy radiation crosslinking of organopolysiloxane.

6. A composition according to claim 1, wherein the resin-coated silicone elastomer is obtained by a process comprising a crosslinking addition reaction (A) of diorganopolysiloxane containing at least two hydrogens each bonded to a silicon, and (B) of diorganopolysiloxane containing at least two ethylenically unsaturated groups bonded to silicon, optionally in the presence (C) of a platinum catalyst.

7. A composition according to claim 1, wherein the resin-coated silicone elastomer is obtained by a process comprising reaction of dimethylpolysiloxane with dimethylvinylsiloxy end groups and of methylhydrogenopolysiloxane with trimethylsiloxy end groups, in the presence of a platinum catalyst.

8. A composition according to claim 1, wherein the resin-coated silicone elastomer is a non-emulsifying elastomer.

9. A composition according to claim 1, wherein the silicone elastomer powder is coated with silsesquioxane resin.

10. A composition according to claim 1, wherein the at least one low molecular weight $C_{10}$ to $C_{25}$ ester oil is not a volatile oil.

11. A composition according to claim 1, wherein the at least one low molecular weight $C_{10}$ to $C_{25}$ ester oil is at least one selected from the group consisting of, a hydroxylated ester, a neopentanoic acid ester, an isononanoic acid ester, an isopropyl alcohol ester, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof.

12. A composition according to claim 1, comprising at least two different low molecular weight $C_{10}$ to $C_{25}$ ester oils.

13. A composition according to claim 1, wherein said at least one wax is chosen from:
beeswax, lanolin wax and Chinese insect waxes; rice wax, carnauba wax, candelilla wax, ouricury wax, cork fibre wax, sugarcane wax, Japan wax and sumach wax; montan wax, microcrystalline waxes, paraffin waxes, ozokerites, ceresin wax, lignite wax, polyethylene waxes, fatty acid esters and glycerides that are solid at 40° C., the waxes obtained by catalytic hydrogenation of animal or plant oils containing linear or branched C8-C32 fatty chains, silicone waxes, fluoro waxes, and mixtures thereof.

14. A composition according to claim 1, wherein said at least one wax is chosen from carnauba waxes and microcrystalline waxes, and mixtures thereof.

15. A composition according to claim 1, wherein the at least one dyestuff is chosen from pigments, nacres and flakes, and mixtures thereof.

16. A composition according to claim 1, further comprising at least one spherical filler, other than the resin-coated silicone elastomer powder.

17. The solid anhydrous cosmetic composition according to claim 1, wherein:
the at least one silicone elastomer is an elastomer corresponding to the INCI name "dimethicone/vinyl dimethicone crosspolymer", and
the at least one silicone elastomer powder is an elastomer powder corresponding to the INCI name "dimethicone/methicone silsesquioxane crosspolymer".

18. A process for making up keratin materials, comprising applying to the keratin materials the solid anhydrous cosmetic composition according to claim 1.

19. The composition according to claim 1, wherein said composition comprises from 1 to 6% by weight, based on the total weight of the composition, of the at least one silicone elastomer powder coated with a silicone resin.

20. The composition according to claim 1, wherein said composition comprises from 2 to 7% by weight, based on the total weight of the composition, of the at least one non-spherical silicone elastomer.

21. The composition according to claim 1, wherein said composition comprises from 20-55% by weight, based on the total weight of the composition, of the at least one low molecular weight $C_{10}$ to $C_{25}$ ester oil.

* * * * *